United States Patent
Ripart et al.

(10) Patent No.: US 6,622,039 B1
(45) Date of Patent: Sep. 16, 2003

(54) ACTIVE IMPLANTABLE MEDICAL DEVICE HAVING RESYNCHRONIZED CARDIAC STIMULATION FOR THE TREATMENT OF CARDIAC INSUFFICIENCY

(75) Inventors: Alain Ripart, Gif-sur-Yvette (FR); Anne Bouhour, Ville-d'Avray (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 09/589,339

(22) Filed: Jun. 7, 2000

(30) Foreign Application Priority Data

Jun. 11, 1999 (FR) .................................... 99 07388

(51) Int. Cl.[7] ............................................ A61N 1/362
(52) U.S. Cl. ....................................................... 607/9
(58) Field of Search ........................... 607/14, 9, 17, 607/19, 4, 5, 27, 28

(56) References Cited

U.S. PATENT DOCUMENTS

| | | | | |
|---|---|---|---|---|
| 4,344,437 A | * | 8/1982 | Markowitz | 607/9 |
| 4,856,521 A | * | 8/1989 | Irnich | 607/17 |
| 4,945,909 A | * | 8/1990 | Fearnot et al. | 607/14 |
| 5,609,613 A | * | 3/1997 | Woodson et al. | 607/19 |
| 5,882,352 A | * | 3/1999 | Duncan et al. | 607/4 |
| 6,021,350 A | * | 2/2000 | Mathson | 607/17 |
| 6,047,213 A | * | 4/2000 | Sirokman et al. | 607/9 |

* cited by examiner

*Primary Examiner*—George R. Evanisko
(74) *Attorney, Agent, or Firm*—Orrick, Herrington & Sutcliffe LLP

(57) ABSTRACT

An active implantable medical device, in particular a pacemaker, defibrillator and/or cardiovertor of the multisite type, having an improved resynchronized cardiac stimulation capability for the treatment of cardiac insufficiency in which the maximum stimulation frequency Fmax is gradually increased over time, starting from an initial value of $F_0$ up to a target value of $F_1$. Moreover, when the device shortens the atrio-ventricular delay as the instantaneous heart rate increases, the device also compares the instantaneous heart rate with a predetermined threshold, and allows the reduction of the atrio-ventricular delay only when the instantaneous heart rate is below this predetermined threshold, and gradually increases the atrio-ventricular delay as the instantaneous heart rate increases above the threshold.

5 Claims, 2 Drawing Sheets

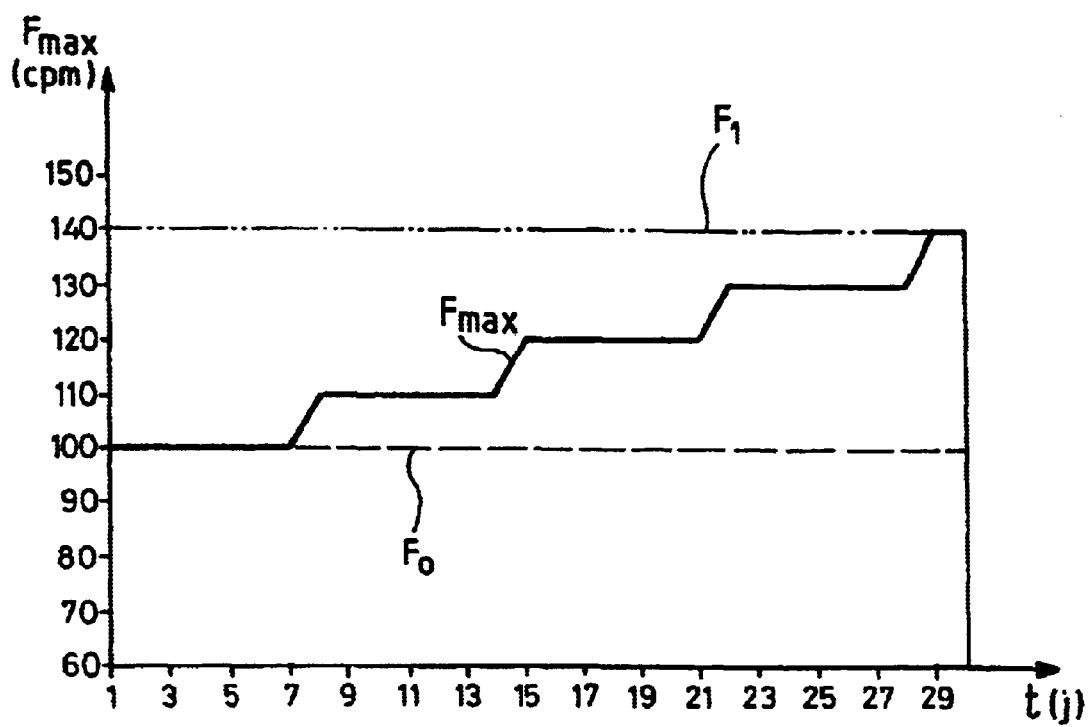

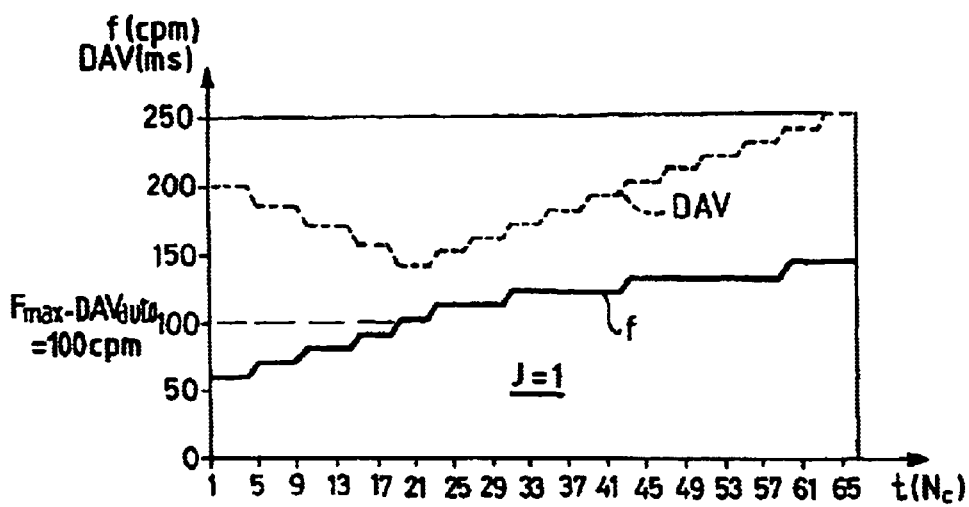
FIG_2
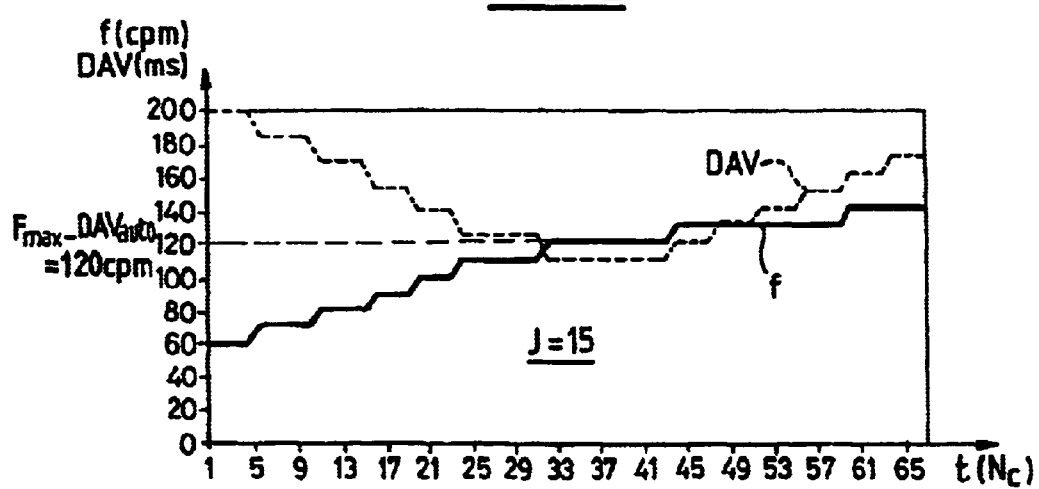
FIG_3
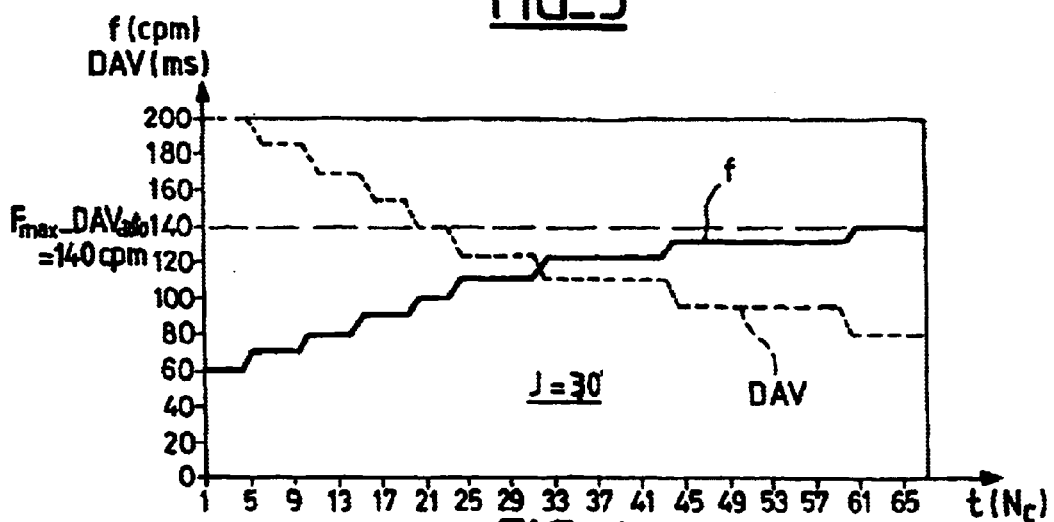
FIG_4

ACTIVE IMPLANTABLE MEDICAL DEVICE HAVING RESYNCHRONIZED CARDIAC STIMULATION FOR THE TREATMENT OF CARDIAC INSUFFICIENCY

FIELD OF THE INVENTION

The present invention relates to "active implantable medical devices" as defined by the Jun. 20, 1990 Directive 09/385/CEE of the Council of the European Communities, as it relates to pacemakers, defibrillators and/or cardiovertors that are able to deliver low energy pulses to the heart for the treatment of heart rate disorders. This invention more particularly relates to prostheses known as "multisite devices" in which electrodes are respectively placed in distinct sites comprising at least one ventricular site and at least one atrial site. Examples of such multisite type prostheses include a "dual chamber" prosthesis, e.g., a pacemaker capable of right atrial stimulation and right ventricular stimulation, a "triple chamber" prosthesis, e.g., right atrial stimulation and double (left and right) ventricular stimulation, and a "quadruple chamber" prosthesis, e.g., double atrial stimulation and double ventricular stimulation.

BACKGROUND OF THE INVENTION

It has been proposed that, in addition to the treatment of heart rate disorders, myocardial contractions in patients suffering from cardiac insufficiency may be treated by stimulation. This is so whether the myocardial contraction disorders are spontaneous or induced by a traditional stimulation. The studies of J. C. Daubert et al., *Stimucoeur*, no. 3, pp. 170–176, which give a complete report on this subject, can serve as a point of reference in this matter.

It was, in particular, a proposal to switch to stimulating simultaneously the left and right ventricles for the resynchronization of cardiac activity which made it possible to observe frequently results that were quite spectacular for patients suffering from a Class III cardiac insufficiency, especially for those patients who did not benefit from more traditional treatments. The patient obtains an instantaneous benefit from such a treatment, resulting in the patient's having a renewed gusto for life and, in certain cases, allowing the patient the possibility of partaking again in activities that were heretofore impossible. However, as the patient's cardiovascular system is not rehabilitated as rapidly as the cardiac sufficiency can be improved, and does not have sufficient time to adjust to improved cardiac sufficiency, the resumption of an almost normal lifestyle by the patient can often place very taxing demands upon what is still a fatigued and ill heart.

However, in these circumstances, the physician neither can limit the capacity of effort of the patient (also called "effort capacity"), i.e., restrict the amount of exertion undertaken by the patient for too lengthy a period, which would effectively reduce the effectiveness of the device, nor reexamine the patient at shorter intervals.

OBJECTS AND SUMMARY OF THE INVENTION

It is an object of the present invention to remedy the problems outlined above by providing the patient with a progressive effort capacity, which capacity evolves automatically over time.

Broadly, the present invention proposes to adapt a parameter known as "maximum frequency" or "Fmax", which is the maximum follow-up frequency of the atrial rate by the ventricle, i.e., the higher limit to which a pacemaker can synchronize a ventricular stimulation on each atrial detection in a conventional DDD pacing mode. This parameter Fmax is used, in particular, to determine a maximum frequency limit for the stimulation frequency as calculated by a control algorithm, such as the algorithm that implements the functions of rate smoothing or rate control.

In a dual chamber pacemaker, the maximum frequency also serves as a reference value and is compared to the detected atrial frequency in order to limit the ventricular stimulation frequency when the atrial rate exceeds the maximum frequency value, for example, by applying an operating mode called the "Wenckebach" mode. Heretofore, the maximum frequency has been more or less programmed permanently at a predetermined value, selected mainly according to the patient's age, and eventually adjusted to take into account the patient's effort and/or the presence of any cardiopathy or cardiomyopathy.

The invention thus also is directed to a device of the "multisite" type comprising resynchronized cardiac stimulation for the treatment of cardiac insufficiency, characterized in that the invention includes gradually increasing, over a period of time, the maximum frequency of stimulation, from a starting or initial value up to a target value. Preferably, the maximum frequency is gradually increased by successive increments at regular intervals.

In one advantageous embodiment, when the device also comprises means for shortening the atrio-ventricular delay as the instantaneous heart rate increases, the device then also comprises means for comparing the instantaneous heart rate to a predetermined threshold, and means for allowing for the reduction of the atrio-ventricular delay to occur only when the instantaneous heart rate is above the threshold.

In an alternate embodiment, the invention may advantageously comprise means for lengthening the atrio-ventricular delay, which can be gradually lengthened as the instantaneous heart rate increases.

Optionally and advantageously, the value of the predetermined threshold can be gradually raised over time.

BRIEF DESCRIPTION OF THE DRAWINGS

Other characteristics, features and advantages of the present invention will appear to a person of ordinary skill in the art in view of the following detailed description, made with reference to the annexed drawings, in which like reference characters refer to like elements, and in which:

FIG. 1 shows the evolution, over time, of the maximum Fmax frequency adjusted according to the present invention; and FIGS. 2 to 4 illustrate the variation of the atrio-ventricular delay ("AVD") as a function of the instantaneous heart rate in the effort phase at three stages respectively of Fmax.

DETAILED DESCRIPTION OF THE INVENTION

When the physician initially programs, normally at start-up, the prosthesis so as to set up a resynchronized cardiac stimulation, typically a resynchronized ventricular stimulation, the physician programs a certain number of parameters and, in addition, a certain number of parameters that are part of the embodiment of the invention which are (1) an initial value $F_0$, which is the initial value for the term "maximum frequency," (2) an optimal maximum frequency $F_1$, regarded as a desired target value, given the state of the patient, and (3) a time or date (referred to as the "endtime") by which the optimal frequency will be reached. The physician can thus, for example, program a maximum starting frequency $F_0$ of 100 bpm, an optimal maximum frequency $F_1$ of 140 bpm, and an endtime of one month, whereby the frequency maximum will start at $F_0$ and reach the optimal maximum frequency $F_1$ by the endtime of one month. The control software of the pacemaker, which implements the function as described herein, will automatically adjust the value of the maximum frequency ("Fmax") until it reaches the $F_1$ value target at the end of the given endtime. This progressive adjustment can be done, in particular, as illustrated in FIG. 1 corresponding to the values of the numerical example given above, by successive increments, for example, increments of 10 bpm every seven days.

The physiological consequences of this adjustment of the maximum frequency are as follows:

For a patient not having a proper cardiac rhythm, for example, a patient in atrial fibrillation, the patient's effort capacity will be naturally limited by the patient's heart rate. For a patient having a sinusal rate with spontaneous atrioventricular conduction, the heart rate will not be limited, but the resynchronization will stop , i.e., it will not follow the atrial rate, above the maximum frequency when the maximum frequency is reached. The invention is intended, in this case, for very symptomatic patients, who will typically stop their effort immediately and will thus limit their activities. For such patients, this approach also could be supplemented by an anti-arrhythmic drug treatment, which will limit sinusal acceleration.

Another technique which may be used to limit the effort capacity of a patient is, in a manner that also is characteristic of the invention, to modify the AVD in the manner described below. Both techniques are directed to reduce the ventricular frequency when the atrial rate increases too much.

For the resynchronized ventricular stimulation, the AVD is usually adjusted so as to capture 100% of ventricular depolarization. Generally, the AVD varies according to the instantaneous heart rate, typically decreasing when the frequency is increasing.

It is noted that the instantaneous frequency of the patient is either a spontaneous frequency, i.e., sinusal, or a stimulated frequency. The stimulation frequency applied is driven by the pacemaker between a base frequency and a maximum frequency, according to the patient's state of effort.

When the resynchronized stimulation is set up by the physician, the physician programs, in addition to the usual parameters, a value Fmax, which in this embodiment is the "maximum frequency for the adaptation of the AVD", hereinafter "Fmax_AVDauto", with a starting frequency value designated "$F_0$". The physician also programs the target maximum frequency $F_1$ of the patient and an endtime period at the end of which it is expected that the Fmax_AVDauto value will reach the maximum frequency $F_1$. For example, the physician programs a starting Fmax_AVDauto value $F_0$ of 100 bpm and a maximum frequency $F_1$ of 140 bpm, which will be reached at the endtime of one month.

Once programmed, the control function algorithm of the pacemaker will at that point automatically adjust the value of Fmax_AVDauto by the appropriate value, as mentioned in the example given above, at a rate increase of 10 bpm every seven days. The Fmax value, which evolves from Fmax_AVDauto=$F_0$ over a given delay period of time, constitutes a threshold M which controls the way in which the AVD will be modified according to variations of the patient's instantaneous heart rate. As long as the instantaneous heart rate remains below the Fmax_AVDauto threshold, the AVD is modified in the usual way, i.e., it is automatically shortened as the instantaneous heart rate increases, the AVD varying between conventionally established limits "AVDmin" and "AVDmax". On the other hand, as soon as the instantaneous heart rate exceeds the Fmax_AVDauto limit, the AVD will increase gradually, for example, at a rate of 10 ms after every fourth cardiac cycle, such values of the increment and frequency of increment being programmable for a particular patient, until either a ventricular depolarization is detected or an AVDmax limit value is reached.

FIGS. 2 to 4 illustrate the manner in which, in this example, the AVD varies, in dashed lines, expressed in milliseconds, according to the instantaneous heart rate F, in solid lines, expressed in beats per minute (bpm), during a phase of effort. The X-coordinate is time expressed as the number of successive cardiac cycles $N_c$.

It should be understood that in order to better explain the specificity of this characteristic, a constant target value of Fmax has been adopted, which is equal at the outset to the optimal value targets. However, it should also be understood that in practice, the. Fmax and Fmax_AVDauto parameters can each be made to evolve gradually over time, so as to better treat the patient.

The drawings show the way in which the AVD varies for the given example according to the instantaneous heart rate at three stages, respectively:

FIG. 2: at the first day, when Fmax_AVDauto=100 bpm;

FIG. 3: at the fifteenth day, when Fmax_AVDauto=120 bpm; and

FIG. 4: at the thirtieth day, when Fmax_AVDauto=140 bpm.

In these examples, the effort is the same in all three cases, and, additionally, the AVD is limited in any event to the following parameters: AVDmin=80 ms and AVDmax=200 ms.

The present invention is preferably implemented in the form of software which executes a control algorithm controlling the Fmax value, which operates in a traditional microprocessor controlled-type pacemaker or multisite device. The CHORUS brand of pacemakers available from ELA Médical are suitable dual chamber pacemaker devices, which may be configured with the software at the time of manufacture or by downloading software by telemetry into an already implanted device for implementing the invention.

One skilled in the art will appreciate that the present invention can be practiced by other than the described embodiments, and the particular numerical values set forth for those embodiments, which are presented for purposes of illustration and not of limitation.

We claim:

1. In an active implantable medical device having means for resynchronizing atrial and ventricular stimulation for a treatment of cardiac insufficiency, having a maximum stimulation frequency, the improvement comprising means for increasing, over a predetermined time extending over a plurality of cardiac cycles, the maximum stimulation frequency, from an initial value to a target value.

2. In an active implantable medical device having means for resynchronizing atrial and ventricular stimulation for a treatment of cardiac insufficiency, having a maximum stimulation frequency, the improvement comprising means for increasing, over a predetermined time extending over a plurality of cardiac cycles, the maximum stimulation frequency, from an initial value to a target value by a preselected interval in successive increments.

3. In an active implantable medical device having means for resynchronizing atrial and ventricular stimulation for a treatment of cardiac insufficiency, having a maximum stimulation frequency and an adjustable atrio-ventricular delay and means for detecting a heart rate, the improvement comprising means for increasing, over a time, the maximum stimulation frequency, from an initial value to a target value, means for detecting an increase in the heart rate, means for shortening the atrio-ventricular delay as the heart rate increases, and means for comparing the heart rate with a predetermined threshold and for allowing the shortening of the atrio-ventricular delay when the heart rate is below said predetermined threshold.

4. The device of claim 3, wherein the improvement further comprises means for increasing the atrio-ventricular delay as the heart rate increases, when said heart rate is greater than said predetermined threshold.

5. The device of claim 3, wherein the improvement further comprises means for increasing over time said predetermined threshold value.

* * * * *

UNITED STATES PATENT AND TRADEMARK OFFICE
CERTIFICATE OF CORRECTION

PATENT NO. : 6,622,039 B1
DATED : September 16, 2003
INVENTOR(S) : Alain Ripart and Anne Bouhour It is certified that error appears in the above-identified patent and that said Letters Patent is hereby corrected as shown below:

Column 2,
Line 34, delete "above" and insert -- below -- therefor;

Signed and Sealed this

Twenty-second Day of March, 2005

JON W. DUDAS
*Director of the United States Patent and Trademark Office*